United States Patent [19]

Hutson, Jr. et al.

[11] 4,056,577

[45] Nov. 1, 1977

[54] SEPARATION OF ACID-HYDROCARBON EMULSIONS AND ALKYLATION PROCESS UTILIZING SAID SEPARATION

[75] Inventors: Thomas Hutson, Jr.; Donald J. Makovec, both of Bartlesville, Okla.

[73] Assignee: Phillips Petroleum Company, Bartlesville, Okla.

[21] Appl. No.: 741,315

[22] Filed: Nov. 11, 1976

[51] Int. Cl.$^2$ .................... C07C 3/54; B01D 17/04
[52] U.S. Cl. ...................... 260/683.48; 252/344
[58] Field of Search ............ 260/683.48, 683.58, 260/683.59, 683.62, 683.51; 252/344

[56] References Cited

U.S. PATENT DOCUMENTS

| 2,717,913 | 9/1955 | Rollman | 260/683.58 |
| 2,920,124 | 1/1960 | Stiles | 260/683.59 |
| 3,205,169 | 9/1965 | Kirkpatrick et al. | 252/344 |
| 3,231,633 | 1/1966 | Kramer | 260/683.51 |
| 3,371,127 | 2/1968 | Cabanaw et al. | 260/683.43 |
| 3,467,729 | 9/1969 | Rodgers | 260/683.62 |

Primary Examiner—George Crasanakis

[57] ABSTRACT

The time for effecting separation of HF acid-hydrocarbon emulsions is substantially decreased by adding a finite amount of up to about 700 ppm of a tetraalkylammonium iodide coalescing promoter to the emulsion. The rapid separation of HF acid-hydrocarbon emulsions comprising reaction effluent obtained from alkylation processes is facilitated by the addition of a tetraalkylammonium iodide to the reaction effluent prior to phase separation.

9 Claims, No Drawings

SEPARATION OF ACID-HYDROCARBON EMULSIONS AND ALKYLATION PROCESS UTILIZING SAID SEPARATION

This invention relates to an improved process for the separation of HF acid-hydrocarbon emulsions and to the production of high quality alkylate. In accordance with another aspect, this invention relates to an improved recovery system following alkylation for the separation of a hydrocarbon liquid phase and an HF acid catalyst liquid phase comprising the addition of a tetralkylammonium iodide coalescing promoter to decrease the time for effecting phase separation of the alkylation effluent. In accordance with another aspect, this invention relates to minimizing the time a hydrocarbon phase separating from an alkylation reaction mass is in contact with an HF acid phase by addition of a controlled amount of a tetraalkylammonium iodide as a coalescing promoter to the reaction effluent. In accordance with a further aspect, this invention relates to the HF alkylation of isoparaffins with olefin(s) by adding to the alkylation effluent a controlled amount of a tetraalkylammonium iodide coalescing promoter followed by separation of the reaction mass into a hydrocarbon liquid phase and an HF acid catalyst liquid phase in a relatively short period of time due to the presence of the coalescing promoter during phase separation.

It is known in the art to react alkylatable hydrocarbons with alkylating hydrocarbons in the presence of an HF acid catalyst to produce alkylate. The alkylation reaction effluent normally is subjected to gravity separation wherein the mass is allowed to separate in a suitable settling zone into a hydrocarbon liquid phase and an HF acid catalyst liquid phase. The hydrocarbon phase recovered from the settling zone is conventionally subjected to fractionation to recover alkylate, unreacted hydrocarbon, and residual HF. One of the problems encountered in the usual alkylation process is the presence of heavy materials which reduce the quality of the alkylate yielded. The heavy materials produced ordinarily are caused by prolonged contact of the hydrocarbon phase and HF acid phase following alkylation. The present invention overcomes this problem by minimizing the time that the hydrocarbon separating from the reaction mass is allowed to be in contact with the HF phase in the settling zone so that the separating liquid hydrocarbon phase is in contact with the HF acid catalyst after removal from the alkylation zone a very short period of time.

Accordingly, an object of this invention is to provide an improved process for effecting separation of HF acid-hydrocarbon emulsions.

Another object of this invention is to provide an improved process for alkylation.

Another object of this invention is to provide an improved process for the rapid separation of an alkylation effluent into separate hydrocarbon and acid phases.

Other objects, aspects, and the several advantages of this invention will be apparent to those skilled in the art upon a study of the disclosure and the appended claims.

In accordance with the invention, a process is provided for achieving rapid separation of HF acid-hydrocarbon emulsions into separate HF acid and hydrocarbon phases by addition of up to about 700 ppm of a tetraalkylammonium iodide coalescing promoter to the emulsion.

In accordance with another embodiment of the invention, an improved process for the production of high quality motor fuel alkylate is provided which comprises reacting an alkylatable hydrocarbon with an olefin in the presence of an HF acid catalyst, adding to the alkylation effluent a finite amount of up to about 700 ppm of a tetraalkylammonium iodide as a coalescing promoter to minimize the time for the hydrocarbon phase to separate from the alkylation reaction mass, and allowing the alkylation separation effluent to separate into an HF acid phase and a hydrocarbon phase.

In accordance with a specific embodiment of the invention, a process for alkylation recovery of high octane motor fuel alkylate is provided comprising reacting isobutane with butylenes in the presence of an HF acid catalyst under alkylation conditions, adding to the alkylation reaction mass effluent a finite amount of up to about 700 ppm of tetrabutylammonium iodide to decrease the time to effect phase separation of the alkylation effluent, passing the alkylation effluent into a phase separation zone, and allowing the effluent to separate into an upper hydrocarbon phase and a lower acid phase, both of which can be separately withdrawn and passed to further processing as desired.

The conditions for carrying out the alkylation reaction of the present invention are well known in the art. The present invention is directed to improved separation of the alkylation reaction mass by decreasing the time for separation of the hydrocarbon phase and the catalyst phase in a separation zone following alkylation.

In general, any of the conventional catalytic alkylation reactions can be carried out by the method and with the apparatus of the present invention. Thus, the alkylation reaction can comprise the reaction of an isoparaffin with a butylene with the reaction being carried out in the presence of HF acid as the alkylation catalyst. Such conventional alkylation is taught in U.S. Pat. No. 3,213,157.

The alkylation reaction is carried out with the hydrocarbon reactants in the liquid phase; however, the reactants need not be normally liquid hydrocarbons. The reaction conditions can vary in temperature from, say, about $-40°$ F ($-40°$ C) to as high as 150° F (66° C) and carried out under sufficient pressure to maintain liquid phase conditions. While generally applicable to the alkylation of hydrocarbons, the present invention is particularly effective for the alkylation of saturated branched chain paraffins such as isobutane and/or isopentane with butylenes in the presence of hydrofluoric acid. In the alkylation of isoparaffins with butylenes, a substantial molar excess of isoparaffin to butylenes is employed, usually to provide the feed ratio in excess of 1:1, usually from 4:1 to about 20:1, and preferably from about 10:1 to about 15:1. The reaction zone is maintained under sufficient pressure to insure that the hydrocarbon reactants and alkylation catalyst are in the liquid phase. The volume ratio of HF to total hydrocarbons will be in the range of 0.2 to 1 to about 20 to 1.

In accordance with the invention, it has been found that rapid separation of HF acid-hydrocarbon emulsions into separate liquid HF acid and liquid hydrocarbon phases can be achieved by adding to the emulsion a finite amount of up to about 700 ppm of a tetraalkylammonium iodide as a coalescing promoter. Suitable iodide compounds that can be employed include those having alkyl groups from about 4 to about 20 carbon atoms with lower alkyl-substituted compounds (4 to 8 carbon alkyls) presently preferred. Representative examples of suitable tetraalkylammonium iodide compounds include tetrabutylammomium iodide, tetrapentylammonium iodide, tetraoctylammonium iodide, tetrahexadecylammonium iodide, tetraeicosylammonium iodide, tetradodecylammonium iodide, and the like, including mixtures thereof. Presently preferred is tetrabutylammonium iodide and other lower alkylammonium iodides, wherein the alkyl group has 4 to 8 carbon atoms.

The amount of tetraalkylammonium iodide added to the HF acid-hydrocarbon emulsion will be a sufficient finite amount of up to about 700 ppm, based on HF acid present in the emulsion, to cause rapid separation of the HF acid-hydrocarbon emulsion into separate HF acid and hydrocarbon phases. It is presently preferred that the amount of coalescing promoter ranges from about 200 to about 700 ppm with about 700 ppm being preferred when tetrabutylammonium iodide is employed.

In actual operation, in connection with facilitating the separation of an HF acid-hydrocarbon emulsion obtained as by the effluent of an alkylation reaction, the tetraalkylammonium iodide is preferably added to the effluent prior to introduction into a phase separation zone such as a gravity settling or separation zone. If desired, the tetraalkylammonium iodide can be added to the alkylation reaction so as to decrease the time for causing separation between the hydrocarbon and acid phases. Ordinarily, alkylation effluent comprising HF acid catalyst, alkylated hydrocarbons, and unreacted hydrocarbons is passed to a phase separation zone such as a gravity separator wherein the separate hydrocarbon and HF acid phases can form. The coalescing promoter is added to the alkylation reaction effluent ordinarily prior to introduction into the settling zone. As demonstrated by the specific working example hereinbelow, the time for effecting phase separation between the HF acid and hydrocarbons can be decreased by about 40 to about 70 percent using tetraalkylammonium iodide in an amount of up to about 700 parts per million by weight of the HF acid catalyst in the alkylation reaction effluent.

SPECIFIC EXAMPLE

Several emulsions were prepared, each with 100 ml of liquid isooctane and 100 ml of liquid HF acid. The two liquids were agitated together by shaking in a closed container for about 60 seconds at room temperature (about 76° F) for runs below. The agitation was stopped and the time was observed for substantially complete liquid phase separation to occur.

The base runs were made without any additive.

The invention runs were made using tetrabutylammonium iodide (TBAI).

| Tetrabutylammonium Iodide (about 76° F) | Phase Separation Time, Seconds |
| --- | --- |
| Base Runs: | |
| (a) - (1) | 28 |
| (b) - (1) | 30 |
| (c) - (1) | 30 |
| (d) - (2) | 30 |
| Invention Runs: | |
| (d) - (3) with 0.07 gms TBAI | 9 |
| (e) - (3) with 0.07 gms TBAI | 11 |
| (f) - (3) with 0.07 gms TBAI | 12 |
| (g) - (4) with 0.07 gms TBAI | 17 |
| (h) - (4) with 0.07 gms TBAI | 17 |

(1) First base sample checked three times.
(2) Second base sample tested only once.
(3) First invention sample checked three times.
(4) Second invention sample checked twice.

Looking at the runs above, it is seen that phase separation time was decreased by about 40 to 70 percent using TBAI in an amount of about 700 parts per million by weight of the HF acid (catalyst).

We claim:

1. A process for achieving rapid separation of HF acid-hydrocarbon emulsions into separate HF acid and hydrocarbon phases which comprises adding to said emulsion a finite amount of up to about 700 ppm of a tetraalkylammonium iodide coalescing promoter, based on HF acid present in said emulsion, and allowing said emulsion containing said coalescing promoter to separate into an HF acid phase and a hydrocarbon phase.

2. A process according to claim 1 wherein said emulsion is the reaction effluent obtained from the alkylation of an isoparaffin with an olefin in the presence of an HF acid catalyst.

3. A process according to claim 1 wherein the coalescing promoter is tetrabutylammonium iodide and the amount added is in the range of about 200 to about 700 ppm.

4. A process for alkylation and recovery of high octane motor fuel alkylate which comprises:
  a. reacting an isoparaffin with an olefin in the presence of HF acid catalyst under alkylation conditions to produce an alkylation effluent comprising HF acid catalyst, alkylated hydrocarbons, and unreacted hydrocarbons,
  b. adding to said effluent a finite amount of up to about 700 ppm of a tetraalkylammonium iodide coalescing promoter, based on HF acid present in said effluent, to decrease the time to effect phase separation of said effluent,
  c. passing said alkylation effluent containing said coalescing promoter to a separation zone wherein phase separation between the hydrocarbons and acid takes place, forming an upper hydrocarbon phase and a lower acid phase, and
  d. separately withdrawing said hydrocarbon phase from an upper portion of said separation zone and an acid phase from the lower portion of said separation zone.

5. A process according to claim 4 wherein said olefin is propylene and/or butylenes and the amount of coalescing promotor present is in the range of about 200 to about 700 ppm.

6. A process according to claim 4 wherein the isoparaffin is isobutane, the olefin is a mixture of butylenes, and the coalescing promoter is tetrabutylammonium iodide.

7. A process according to claim 4 wherein the coalescing promoter is tetrabutylammonium iodide and the amount present is within the range of about 200 to about 700 ppm.

8. In a process for reacting an olefin with an isoparaffin in the presence of liquid HF acid catalyst which passes through a cyclic path including in series and in open communication a vertical extended reaction zone, a settling zone, a cooling zone, and return to said reaction zone, the steps which comprise:
  a. introducing propylene and/or butylenes, isobutane, and HF acid catalyst into a lower portion of said reaction zone and allowing the reaction mixture thus formed to rise through said reaction zone under alkylation conditions and form a reaction effluent,
  b. adding to said effluent a finite amount of up to about 700 ppm of a tetraalkylammonium iodide coalescing promoter, based on HF acid present in said effluent, to decrease the time to effect phase separation c. passing said alkylation reaction effluent containing said coalescing promoter from an upper portion of said reaction zone into a lower portion of a separation zone and allowing said effluent to separate into an upper hydrocarbon phase and a lower HF acid phase, d. withdrawing a hydrocarbon phase from an upper portion of said settling zone and passing same to further separation, and e. withdrawing an HF acid phase from a lower portion of said settling zone below the level of said HF acid phase and passing same through said cooling zone and then introducing the cooled HF acid into a lower portion of said reaction zone for contact with propylene and/or butylenes and isobutane in step (a).

9. A process according to claim 8 wherein the coalescing promoter is tetrabutylammonium iodide and the amount present ranges from about 200 to about 700 ppm.

* * * * *